(12) United States Patent
Smith et al.

(10) Patent No.: US 7,319,400 B2
(45) Date of Patent: Jan. 15, 2008

(54) METHOD AND APPARATUS FOR MONITORING A RESTRAINT DEVICE

(75) Inventors: Toby E. Smith, Broken Arrow, OK (US); Craig L. Cooper, Inola, OK (US); Sanford G. Fitzgerald, Tulsa, OK (US)

(73) Assignee: Bed-Check Corporation, Tulsa, OK (US)

( * ) Notice: Subject to any disclaimer, the term of this patent is extended or adjusted under 35 U.S.C. 154(b) by 266 days.

(21) Appl. No.: 10/966,986

(22) Filed: Oct. 15, 2004

(65) Prior Publication Data

US 2005/0083207 A1 Apr. 21, 2005

Related U.S. Application Data

(60) Provisional application No. 60/512,042, filed on Oct. 17, 2003.

(51) Int. Cl.
*G08B 23/00* (2006.01)
(52) U.S. Cl. .................... 340/573.1; 340/668
(58) Field of Classification Search ............. 340/573.1, 340/573.7, 575, 665, 668, 539.12
See application file for complete search history.

(56) References Cited

U.S. PATENT DOCUMENTS

| | | | |
|---|---|---|---|
| 3,980,988 A | 9/1976 | Spizzo | |
| 4,007,733 A | 2/1977 | Celeste et al. | |
| 4,179,692 A | 12/1979 | Vance | |
| 4,295,133 A | 10/1981 | Vance | |
| 4,298,863 A | 11/1981 | Natitus et al. | |
| 4,417,572 A | 11/1983 | Green | |
| 4,432,599 A | 2/1984 | McMahon | |
| 4,484,043 A | 11/1984 | Musick et al. | |
| 4,565,910 A | 1/1986 | Musick et al. | |
| 4,608,973 A | 9/1986 | Green et al. | |
| 4,611,378 A | 9/1986 | Caserta et al. | |
| 4,700,180 A | 10/1987 | Vance | |
| 4,777,944 A | 10/1988 | Green et al. | |

(Continued)

FOREIGN PATENT DOCUMENTS

GB 2020012 A 11/1979

(Continued)

OTHER PUBLICATIONS

Printed Results of NEARAC Patent Search of Jul. 17, 2004.

*Primary Examiner*—John Tweel, Jr.
(74) *Attorney, Agent, or Firm*—Fellers, Snider, Blankenship, Bailey & Tippens, P.C.; Terry L. Watt

(57) ABSTRACT

The instant invention is designed to detect when undue tension is placed on a belt or strap that is connected to a restraining vest, such undue pressure being indicative that a patient may be in trouble. It is preferable that, whatever sensor is used, it should be elastically resilient to return to its unstressed state after tension on the strap is removed. Additionally, it is preferable that the amount of force that is required in order to trigger an alarm be adjustable to accommodate patients of different weights. Finally, it is also preferable that the level of stress on the strap—and the duration over which it is applied—that is necessary to trigger an alarm be such that the patient cannot easily intentionally cause the device to sound an alarm.

10 Claims, 8 Drawing Sheets

U.S. PATENT DOCUMENTS

| | | |
|---|---|---|
| 4,848,871 A | 7/1989 | Seidel et al. |
| 4,972,177 A | 11/1990 | Nolan |
| 5,224,496 A | 7/1993 | Palmer et al. |
| 5,263,497 A | 11/1993 | Grabenkort et al. |
| 5,353,793 A | 10/1994 | Boran |
| D361,462 S | 8/1995 | Newham |
| 5,494,002 A * | 2/1996 | Greene ................. 340/668 |
| 5,554,835 A | 9/1996 | Newham |
| 5,600,108 A | 2/1997 | Newham |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,945,914 A | 8/1999 | Holmes et al. |
| 6,065,727 A | 5/2000 | Fitzgerald et al. |
| 6,111,509 A | 8/2000 | Holmes |
| 6,292,102 B1 | 9/2001 | Smith |
| 6,307,476 B1 | 10/2001 | Smith et al. |
| 6,417,777 B2 | 7/2002 | Fitzgerald et al. |
| 6,441,742 B1 | 8/2002 | Lovely et al. |
| 6,544,200 B1 | 4/2003 | Smith et al. |
| 6,696,653 B1 | 2/2004 | Smith et al. |
| 6,772,764 B2 * | 8/2004 | Chapman ................. 128/870 |
| 6,784,797 B2 | 8/2004 | Smith et al. |

FOREIGN PATENT DOCUMENTS

| | | |
|---|---|---|
| GB | 2283567 A | 5/1995 |

* cited by examiner

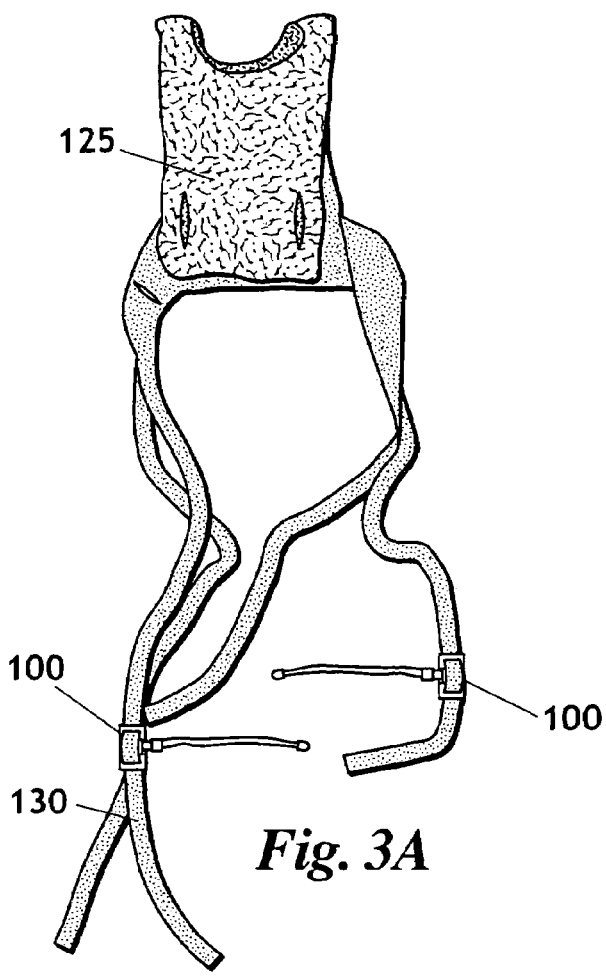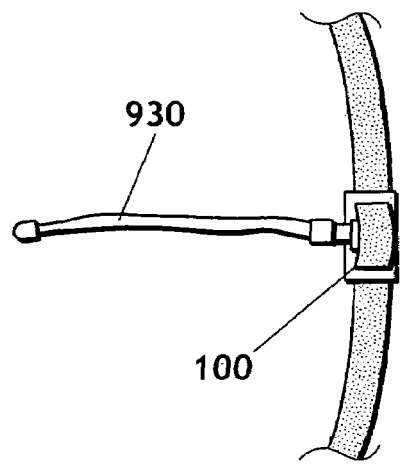
*Fig. 3A*
*Fig. 3C*
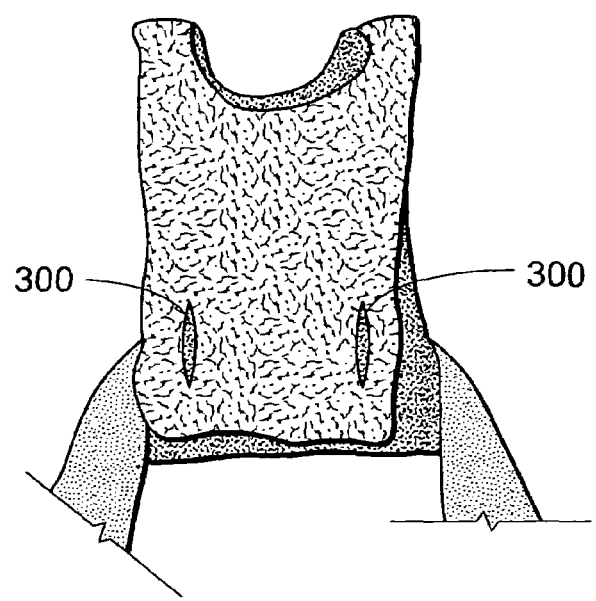
*Fig. 3B*

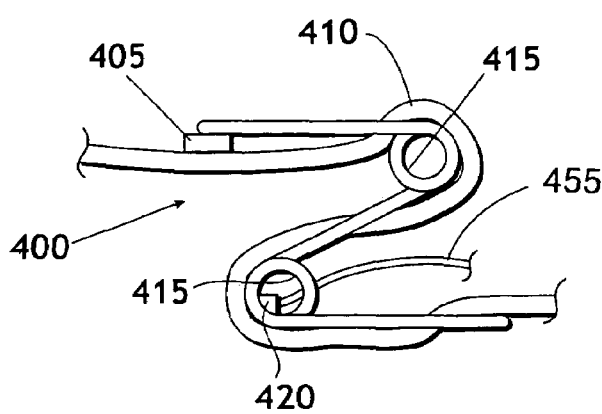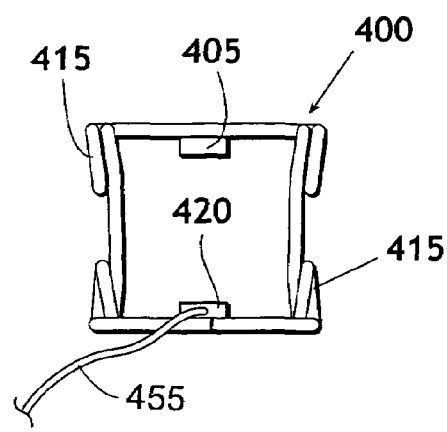
*Fig. 4A*  *Fig. 4B*
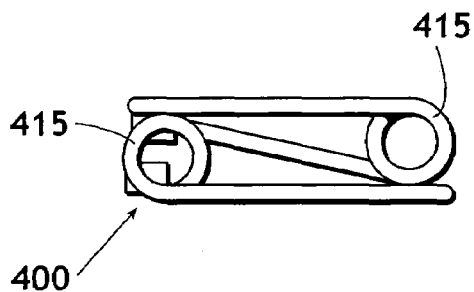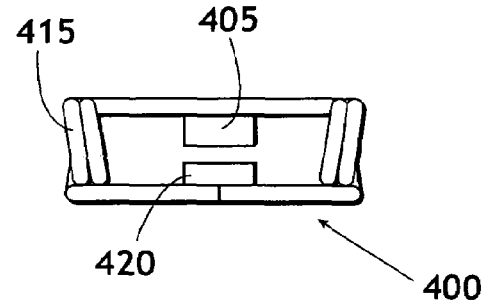
*Fig. 4C*  *Fig. 4D*
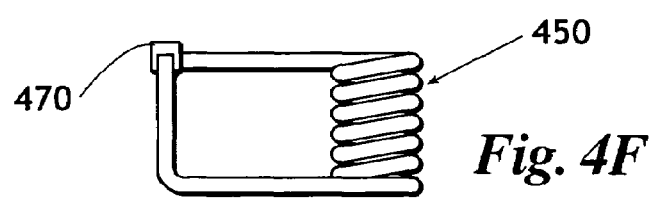
*Fig. 4F*
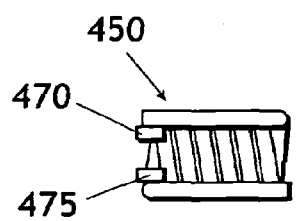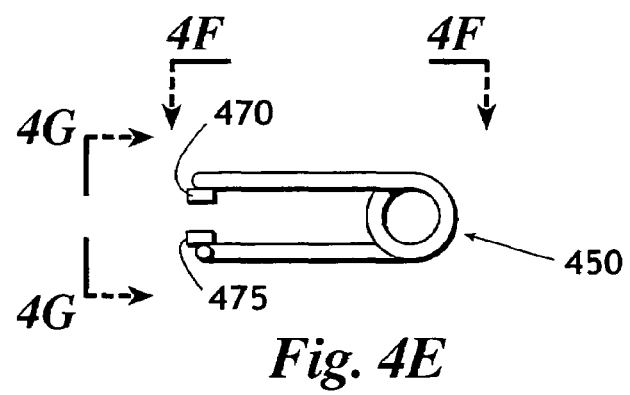
*Fig. 4G*  *Fig. 4E*

METHOD AND APPARATUS FOR MONITORING A RESTRAINT DEVICE

CROSS REFERENCE TO RELATED APPLICATION

This invention claims benefit of co-pending U.S. Provisional Application Ser. No. 60/512,042, filed Oct. 17, 2003.

FIELD OF THE INVENTION

This invention relates generally to monitoring systems and more particularly concerns electronic devices and systems that are used to monitor seated or lying patients in homes or in medical environments such as hospitals, institutions, and other care-giving environments, wherein such monitors employ an alarm to notify a caregiver if the patient's condition changes.

BACKGROUND OF THE INVENTION

It is well documented that the elderly and post-surgical patients are at a heightened risk of falling. These individuals are often afflicted by gait and balance disorders, weakness, dizziness, confusion, visual impairment, and postural hypotension (i.e., a sudden drop in blood pressure that causes dizziness and fainting), all of which are recognized as potential contributors to a fall. Additionally, cognitive and functional impairment, and sedating and psychoactive medications are also well recognized risk factors.

A fall places the patient at risk of various injuries including sprains, fractures, and broken bones—injuries which in some cases can be severe enough to eventually lead to a fatality. Of course, those most susceptible to falls are often those in the poorest general health and least likely to recover quickly from their injuries. In addition to the obvious physiological consequences of fall-related injuries, there are also a variety of adverse economic and legal consequences that include the actual cost of treating the victim and, in some cases, caretaker liability issues.

In the past, it has been commonplace to treat patients that are prone to falling by limiting their mobility through the use of restraints, the underlying theory being that if the patient is not free to move about, he or she will not be as likely to fall. However, research has shown that restraint-based patient treatment strategies are often more harmful than beneficial and should generally be avoided—the emphasis today being on the promotion of mobility rather than immobility. Among the more successful mobility-based strategies for fall prevention include interventions to improve patient strength and functional status, reduction of environmental hazards, and staff identification and monitoring of high-risk hospital patients and nursing home residents.

Additionally, and as is well known to those of ordinary skill in the art, patients are occasionally restrained for reasons not related to the likelihood of a fall including, for example, cases where the patient is unusually agitated or presents a threat to himself or herself, or to the staff.

However, patients who are physically restrained, though they might be protected against certain risks, are now at risk of death or other serious injury which can be brought about because of the circumstances of their confinement. For example, in a typical arrangement, a specialized poncho or vest which is slipped over the patient's head and their arms are extended through the openings provided. Then, straps which extend from the sides of the vest are threaded through slots in the front of the vest, after which the straps are securely tied to the bed frame or other stationary object. In some cases the back of the restraint device may have additional tie points for use with the straps provided or for use with other restraint device. Unfortunately, a patient who is agitated or deluded may slide through or climb over the bed railing and, because of the restraints, be held helpless above the ground unable to return to the bed. Asphyxiation, strangulation, or cardiac arrest can follow in short order.

Of course, if the patient is restrained within a wheelchair similar problems can arise. In some cases the patient can slip downward in the chair so that he or she is at least partially supported by the restraint straps that are tied to the chair frame and left suspended over the front of the chair. In other instances, the chair might tip over and the restraint will work to trap the patient underneath the chair.

It is well known that one proven method of reducing the incidence of injuries and deaths to restrained patients is careful monitoring by the caregiver. However, monitoring of high-risk patients, as effective as that care strategy might appear to be in theory, suffers from the obvious practical disadvantage of requiring additional staff if the monitoring is to be in the form of direct observation. Thus, the trend in patient monitoring has been toward the use of electrical devices to signal changes in a patient's circumstance to a caregiver who might be located either nearby or remotely at a central monitoring facility, such as a nurse's station. The obvious advantage of an electronic monitoring arrangement is that it frees the caregiver to pursue other tasks away from the patient. Additionally, when the monitoring is done at a central facility a single person can monitor multiple patients which can result in decreased staffing requirements.

Thus, what is needed is an electronic patient monitor that can be used to sense when a restrained patient may be in trouble and sound an alarm to summon a caregiver to his or her aid. Additionally, an automated method of sensing the orientation of the wheelchair is needed, so that if a wheelchair tips over an alarm sounds to notify a caregiver of the plight of the occupant.

General information relating to mat-type sensors, electronic monitors and other hardware for use in patient monitoring is relevant to the instant disclosure and may be found in U.S. Pat. Nos. 4,179,692, 4,295,133, 4,700,180, 5,600,108, 5,633,627, 5,640,145, and, 5,654,694, U.S. patent application Ser. Nos. 10/701,581 and 10/617,700, U.S. Pat. Nos. 6,111,509, 6,441,742, and 6,784,797 (the last three of which concern electronic monitors generally). Additional information may be found in U.S. Pat. Nos. 4,484,043, 4,565,910, 5,554,835, 5,623,760, 6,417,777, U.S. patent application 60/488,021, (sensor patents) and U.S. Pat. Nos. 5,065,727 and 6,065,727 (holsters for electronic monitors), the disclosures of all of which aforementioned patents are all incorporated herein by reference as if fully set out at this point. Further, U.S. Pat. No. 6,307,476 (discussing a sensing device which contains a validation circuit incorporated therein), U.S. Pat. No. 6,544,200, (for automatically configured electronic monitor alarm parameters), U.S. Pat. No. 6,696,653 (for a binary switch and a method of its manufacture), and U.S. patent application Ser. No. 10/125,059 (for a lighted splash guard) are similarly incorporated herein by reference.

Additionally, sensors other than mat-type pressure sensing switches may be used in patient monitoring including, without limitation, temperature sensors, patient activity sensors, patient location sensors, bed-exit sensors, toilet seat sensors (see, e.g., U.S. Pat. No. 5,945,914), wetness sensors (e.g., U.S. Pat. No. 6,292,102), decubitus ulcer sensors (e.g., U.S. Pat. No. 6,646,556), etc., all of which are incorporated herein by reference. Thus, in the text that follows the terms "mat" or "patient sensor" should be interpreted in its broadest sense to apply to any sort of patient monitoring switch or device, whether the sensor is pressure sensitive or not.

Finally, pending U.S. patent application Ser. No. 10/397,126, discusses how white noise can be used in the context of decubitus ulcer prevention and in other contexts, and U.S. Patent Application Ser. No. 60/543,718 teaches the use of medical feedback systems to reduce the risk of decubitus ulcer or pressure sore formation. Both of these references are similarly fully incorporated herein by reference.

Heretofore, as is well known in the patient monitoring arts, there has been a need for an invention to address and solve the above-described problems. Accordingly, it should now be recognized, as was recognized by the present inventors, that there exists, and has existed for some time, a very real need for such a system for monitoring patients.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a patient sensor and alarm device that senses and responds to abnormal levels of tension in the straps of a conventional (e.g., vest- or poncho-type, single-limb, etc.) restraint and generates an alarm to warn the caregiver that the patient may be in danger. In another preferred arrangement there is provided an attitude or tilt sensor for use on a wheelchair or similar support device which will determine whether or not the chair is vertically oriented and, if it is not, will send a signal to an attached patient monitor which will result in the generation of an alarm signal.

In more particular, according to an aspect of the instant invention a sensor is provided that is designed to detect when undue tension is placed on a belt or strap that is connected to a restraint device, such undue tension being indicative that a patient may be in distress. It is important for purposes of the instant invention that whatever sensor is used, it is preferably at least somewhat elastically resilient to return to its unstressed state after tension on the strap has been released. Additionally, it is preferable that the amount of force that is required in order to trigger an alarm be adjustable to accommodate patients of different weights. Finally, it is also preferable that the level of stress on the belt—and the duration over which it is applied—that is necessary to trigger an alarm be such that the patient cannot easily intentionally cause the device to sound an alarm. Thus, it is anticipated that a fairly substantial spring element will be used and/or the software that is resident in the attached monitor will be designed to only trigger an alarm in the event of a sustained (as opposed to transitory) engagement of the switch that is positioned on the belt.

According to a first preferred embodiment, one or more of a patient's restraint belts are threaded through a "Z" shaped spring arrangement, so that when tension on the subject belt will tend to spread apart the arms of the "Z". If a reed switch or similar proximity or contact switch suitable for sensing when the arms of the "Z" are separated is incorporated therein, it will be possible for a separate patient monitor to sense the reaction of this embodiment to tension on the straps and summon help if that is needed.

According to another preferred embodiment, a spring arrangement with two arms—similar in general configuration to a clothespin-type spring—is provided which tends to open when a belt that is threaded therethrough is placed under tension. Any number of different sensors might be employed to sense this action and communicate a signal representative thereof to an attached electronic monitor.

In still another preferred arrangement, a belt tension sensor has been provided which is designed to be placed in-line with a belt from the restraint device. That is, the belt which is to be monitored is affixed to one end of the sensor and a separate connection on the other end of the sensor is affixed to the bed frame or other immobile object. The application of tension to a belt from the patient's end will spread an internal spring, the movement of which is sensed and communicated, preferably electronically, to an external monitor.

In another preferred arrangement, there is provided a belt tension sensor that utilizes a pressure sensitive switch which is engaged when tension is placed on a patient restraint belt. More particularly, in a preferred arrangement a rigid base plate is surmounted by a pressure sensitive switch which is arranged such that tension in a belt which is threaded through the base plate exerts pressure against the sensitive switch, thereby opening it and making it possible for a separate patient monitor to sense that a patient may be in trouble. Preferably, a resilient or elastic actuator will be positioned between the belt and the pressure sensitive switch which will, among other things, allow the designer some degree of control over the tensions which will activate the alarm.

In still another preferred arrangement, an embodiment is provided that measures the amount of longitudinal stretching in a restraint belt or strap as an indicator of applied tension. One embodiment utilizes optically transmissive elements to measure the displacement between two fixed points on the belt which is occasioned by stretching due to tension.

Finally, in another preferred embodiment there is provided an inclinometer or similar sensor which can sense the attitude of a wheel chair or other patient support surface and, when the monitored surface is no longer in an upright orientation, communicate that fact to an attendant monitor. Thus, if, for example, a patient tips over in his or her wheel chair—whether or not the patient is restrained—an electronic patient monitor will be able to sense that fact and notify a caregiver. In one preferred arrangement, this sensor will be used in conjunction with those discussed previously to identify situations where a wheel chair has tipped over and a restrained patient is "hanging" beneath the overturned chair.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to apply to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which:

FIGS. 3A-3C contain an illustration of a conventional vest-type restraint device wherein a preferred tension sensor has been attached thereto.

FIGS. 4A-4G contain a schematic illustration of two preferred embodiments of the instant invention, one of which utilizes a "Z" type spring and the other which utilizes a clothespin-type spring.

DETAILED DESCRIPTION OF THE INVENTION

General Environment of the Invention

Figure 1:
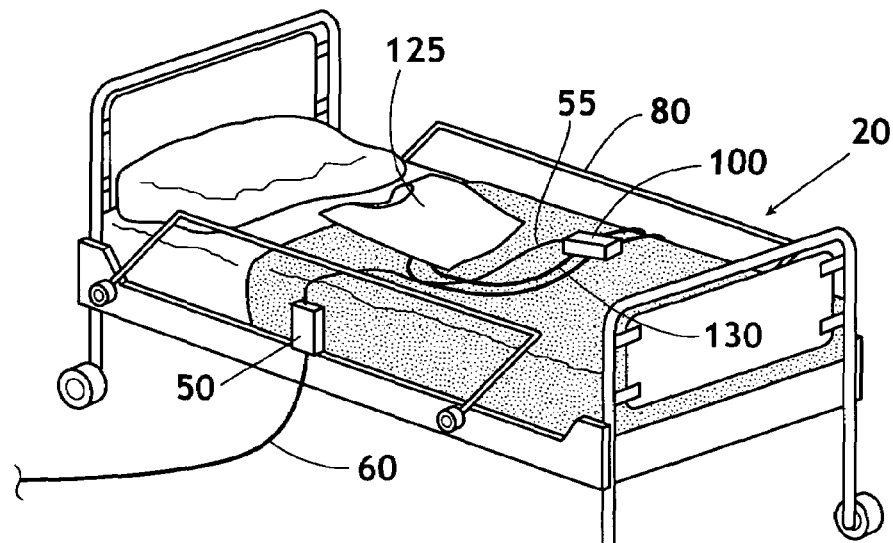
FIG. 1 illustrates the general environment of the instant invention, wherein an electronic patient monitor is connected to a sensor embodiment of the instant invention.
Figure 16:
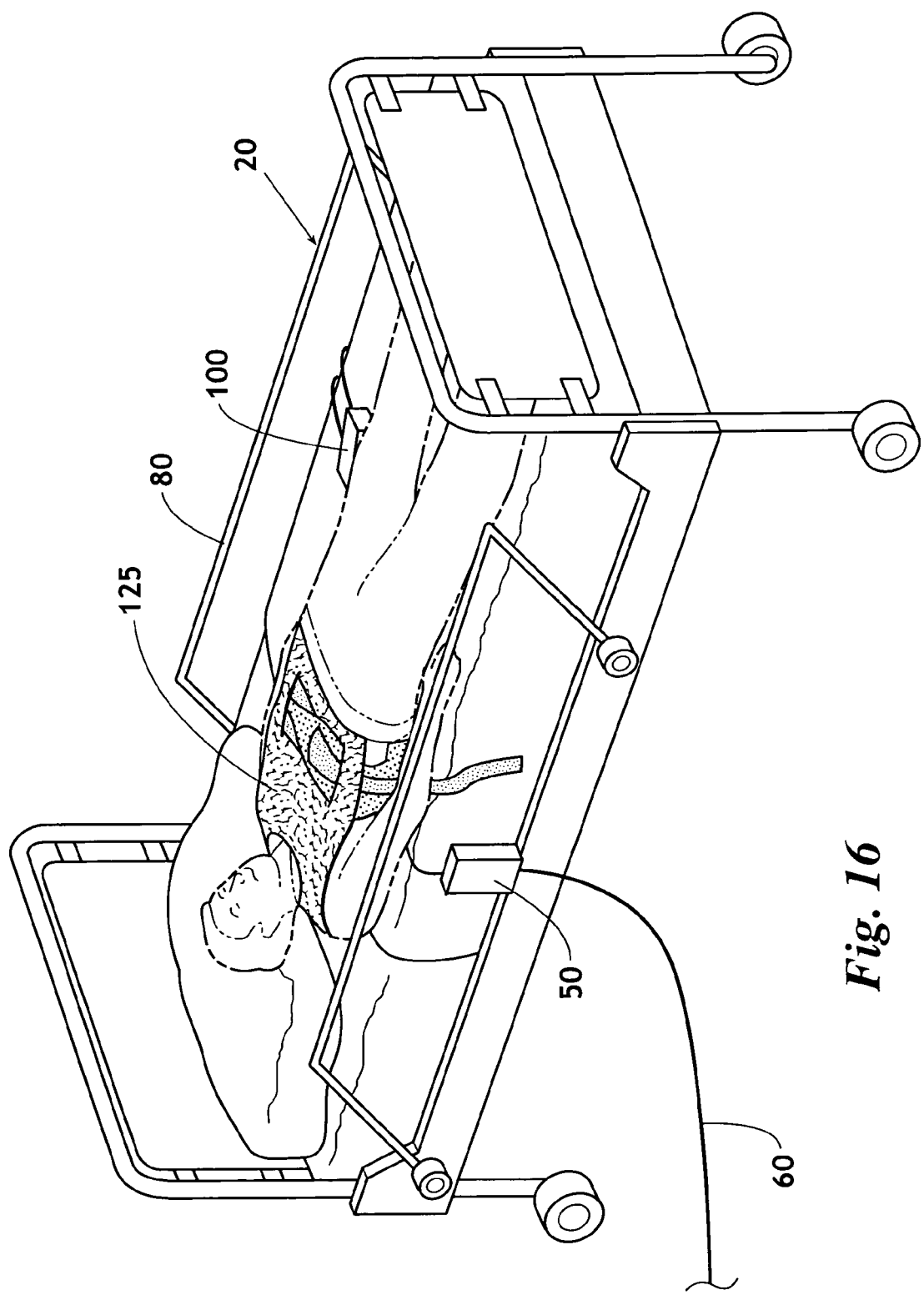
FIG. 16 contains an illustration of a patient in a bed who is wearing a restraint device.

Generally speaking, electronic patient monitors of the sort discussed herein work by first sensing an initial status of a patient, and then generating a signal when that status changes (e.g., the patient changes position from laying or sitting to standing, the sensor changes from dry to wet, a temperature spike occurs, etc.) or if it fails to change (e.g., if the patient has not moved within some predetermined time period). Turning now to FIGS. 1 and 16 wherein the general environment of one specific embodiment of the instant invention is illustrated, in a typical arrangement the instant invention 100 sensor is placed on at least one strap 130 of a patient restraint device 125, preferably there will be a sensor on each side of the patient, thereby monitoring against unintentional egress on either side. Note that, the fastening mechanism of the restraint device 125 (i.e., strap 130 in FIG. 1) might alternatively be called a belt, a tie, etc., by those of ordinary skill in the art. That being said, for purposes of the instant disclosure the term "strap" will be broadly interpreted to include a strap of the sort illustrated in FIG. 1, as well as any similar means for anchoring the restraint device to an immobile object. Often, the patient will be confined to a hospital bed 20 which is generally equipped with side rail 80.

Generally speaking, the sensor 100/electronic monitor 50 combination works as follows. The vest 125 is placed on the patient and the attached straps 130 are wrapped around the patient and threaded through slots 300 (FIG. 3B). Then, absent use of the instant invention, the ends of the straps 130 are then conventionally attached (e.g., tied) to the bed railing 80 or frame, thereby fixing the patient in place. However, in the circumstance where the instant invention is utilized (and depending on the particular embodiment selected), the straps 130 might be affixed to one end of sensor 100 or conventionally tied or otherwise attached to the bed frame/railing 80 and the sensor 100 affixed thereto (FIG. 1). The sensor 100 is then connected via a communications conduit 55 which might be an electrical line, optical fiber, etc.

Then, the patient monitor 50 is activated, for example, by a manual act on the part of a caregiver, automatically upon detection of an attached sensor 100, etc. Thereafter, if the patient manages to leave the bed or becomes otherwise entangled with the vest 125 or its straps 130, the attached sensor 100 will respond to the tension that is placed on the strap 130, which response will be communicated to the monitor 50. The patient monitor 50, which conventionally contains a microprocessor therein, will then signal the caregiver per its pre-programmed instructions. In some cases, the signal will amount to an audible alarm or siren that is emitted from the unit 50. In other cases, an electronic signal could be sent to a remote nurses/caregivers station via electronic communications line 60 or other wired or wireless communications means well known to those of ordinary skill in the art. Note that additional electronic connections not pictured in this figure might include a monitor power cord to provide a source of AC power although, as generally pictured in this figure, the monitor 50 can certainly be configured to be battery, solar, fuel cell or AC powered, etc.

Figure 2:
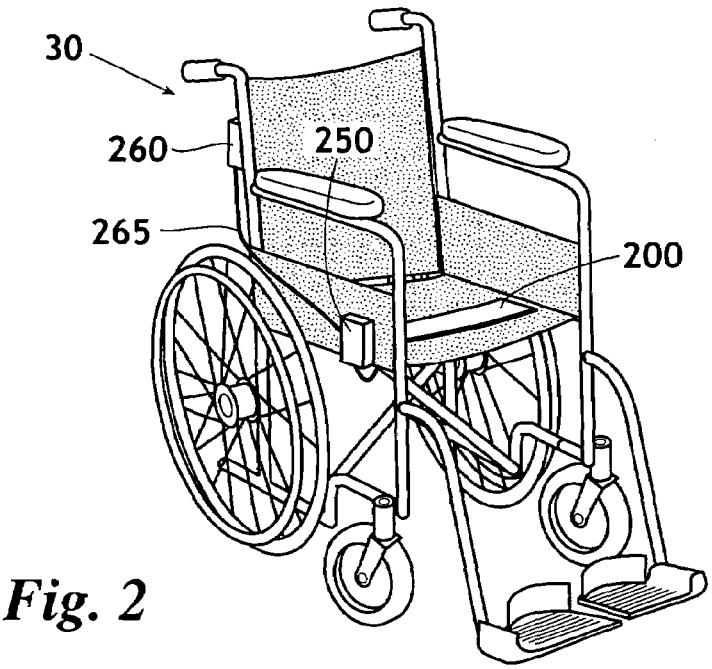
FIG. 2 illustrates a preferred embodiment of the instant wheelchair attitude sensing invention and further including an electronic patient monitor connected to a chair exit mat.

In another common arrangement, and as is illustrated in FIG. 2, a pressure sensitive chair sensor 200 might be placed in the seat of a wheel chair or the like for purposes of monitoring a patient seated therein. Note that the discussion that follows concerning exit mats is also generally applicable to use on a bed or other support surface. A typical exit mat configuration utilizes a pressure sensitive mat 200 that is connected to an electronic chair monitor 250 that is suspended from the chair 30. Because it is anticipated that the patient so monitored might choose to be at least somewhat mobile, the monitor 250 will usually be battery powered and will signal a chair-exit event via an internal speaker, rather than a hardwired nurse-call. Of course, those of ordinary skill in the art will understand that in some instances the monitor 250 will be configured to communicate wirelessly with the nurses' station through IR, RF, ultrasonic or some other communications technology. Additionally, and as is described in greater detail hereinafter, it is preferred that the same electronic monitor 250 be used to monitor the status of attitude sensor 260 which is preferably attached to a rear vertical frame element of the chair 30. Attitude sensor 260 is preferably a mercury or similar switch which responds to changes in tilt (e.g., an accelerometer for sensing relative gravity shifts, movement changes, or angular momentum changes). The sensor 260 is preferably attached to monitor 250 via communications conduit 265 which might be an electrical line, fiber optic cable, etc. Then, if the chair and occupant are tipped over, the sensor 260 will respond to the new orientation and communicate that fact to the attached monitor 250 which will generate an alarm according to its programming. It should be clear that it is certainly possible that tension monitor 100 could be incorporated into this setup in those cases where the patient restraint is affixed to the frame of the wheelchair 30.

According to a first preferred aspect of the instant invention, there is provided a patient sensor for use with an attached patient monitor which is designed to monitor the level of tension in a patient restraint device and, more particularly, which responds to abnormal levels of tension in the straps of a conventional (e.g., vest-type) restraint by generating a signal which is received by an attached monitor alarm to warn the caregiver that the patient may be in danger. Note that the instant invention could potentially be used with any sort of patient restraint device that utilizes a strap that is attached to an immobile object, whether that restraint device is a vest, a single limb restraint, a belt restraint, etc. That being said, for purposes of specificity in the discussion that follows preferred embodiments of the instant invention will be discussed as they might be used in conjunction with the straps of a vest-type restraint. However, it should be understood and remembered that this specificity is purposes of illustration only and the claims that follow should not be so limited.

As is generally set out in FIGS. 1 and 3 and as is well known to those of ordinary skill in the art, a conventional vest- or poncho-type, soft restraint device 125 is placed on the patient and tied about him with the provided waist belt, thereby enclosing the patient within the device. After the vest is in place, the ends of the straps 130 are usually threaded through slits in the front and/or back of the vest through slits 300 that have been provided for that purpose, and then fastened to the bed railings or other permanent fixtures, thereby making it difficult for the patient to move out of the bed. However, such restraints have come under increasing fire for the danger that they can pose. As is well known to those of ordinary skill in the art, a patient may slip down in a wheelchair, or climb over the railing of the hospital bed, etc., thereby putting him or herself at risk of being suspended above the ground by the restraining straps. In an unfortunately not uncommon scenario, the patient who manages to position him or herself outside of the bed or chair while wearing such a restraint may suffer injury or even death due to suffocation or strangulation because of the pressure exerted by the patient's body weight against the restraining device. Patients wearing such devices have strangled and/or been suffocated during a time when the caregiver might be literally only a few yards away.

PREFERRED EMBODIMENTS

In accordance with a first aspect of the instant invention and as is generally indicated in FIG. 1, the instant device preferably works in connection with a conventional patient restraint vest as is indicated in this figure and in FIG. 3. Preferably, the belt 130 from the vest will pass through a sensing device 100 (or be attached to it), the sensor 100 being generally designed to monitor the tension on belt 130. By way of general explanation and as is described in greater details hereinafter, the instant sensing device 100/monitor 50 combination is designed to monitor the tension level in the belt 130 and, if the belt 130 exhibits excessive levels of tension that persist for more than a few seconds (e.g., three seconds or other value selected by the caregiver), the monitor will recognize that condition and signal to a caregiver that the patient is likely in trouble and will need immediate assistance.

Turning now to FIG. 4 which contains a first preferred embodiment of the instant invention, as is indicated in this figure the tension monitoring device 400 is in communication with a separate electronic patient monitor 50 which is designed to read the status of the sensor 400 and, if it is so indicated, generate either a local or a remote alarm in response thereto. It should be noted that one goal of the invention is to eliminate possible false alarms which could arise from a restless patient's straining against the restraint in which he or she has been placed. As a consequence, sensing device 400 will preferably be configured with a spring or other elastic materials so that, when stress is exerted on the belt 410 and then released, the monitoring device 400 will return to its original/unstressed state. It is further preferred that the amount of pressure that is necessary to trigger the alarm 100 will be such that a patient cannot easily manually trigger the alarm by pulling against belt 410. Electrical line 455 provides communication between switch 420 and a separate electronic patient monitor 50. That being said, electrical connectivity is just a preferred means of enabling a communications conduit between monitor 50 and sensor 420 and optical or any other communications medium could readily be adapted to function in the role of the electrical line 455.

In the embodiment of FIG. 4A a strap 410 from the vest 125 is passed through a Z-shaped spring arrangement 400 as is generally indicated in that figure. Note that, for purposes of illustration, the Z-shaped spring device 400 has been expanded so that the method by which the belt is threaded therethrough may be more readily seen. In FIG. 4C, the compressed device 400 is shown. FIG. 4C illustrates the embodiment of FIG. 4A without belt 410, in which case the springs 415 have "compressed" the device 400 to its unstressed configuration. Note that one end of the belt 410 is affixed to the vest 125 and the other end to a stationary object such as a bed frame or bed rail 80.

Turning next to FIG. 4B, this figure contains an end view of the embodiment of FIG. 4A which illustrates more clearly the preferred sensing components of the instant sensor 400. When the device 400 encloses a belt 130 that is not under tension, the sensor pair 405/420 will be proximate to each other. In various preferred embodiments the sensor/receiver pair 405/420 will be, for example, a magnetic pair, a Hall effect device, a contact switch, an optical switch, or other proximity sensing sensor pair. In simplest terms, one function of the switch and sensor combination is to detect when the Z-shaped device 400 is in its closed or near closed state.

Note that in this arrangement if tension is applied only briefly to the device 400, it will expand and will then retract into its closed position thus making it possible for an attached patient monitor 50 to distinguish false alarms from life-threatening events. The stiffness of the springs 415 can be any magnitude chosen by the designer. However, preferably these springs will be sufficiently resilient to make it difficult for a patient to inadvertently generate an alarm and will preferably be selected so that the switch 400 requires, for example, tension on the order of 30 to 60 pounds to trigger it.

In the event that the tension on the belt 410 extends/causes the arms of the device 400 to separate for more than a few seconds, for example about 3 to 15 seconds, the attached patient monitor will sense that fact and determine that the patient is likely in need of assistance. Upon making that assistance determination, an alarm will be sounded by the monitor to notify a caregiver that the patient might be in distress.

According to another preferred embodiment and as is illustrated in FIGS. 4E and 4F, there is provided another embodiment 450 which resembles the spring portion of a conventional clothespin in overall general appearance. As has been described previously, the belt 410 will be threaded through this device and when tension is applied to the belt 410, the arms of the device 450 will spring apart, thereby separating the sensor elements 470 and 475 (e.g., a magnet a reed switch, a Hall effect switch, etc.), and making it possible for an attached monitor to sense that fact and trigger an alarm if it proves to be warranted. Of course, those of ordinary skill in the art will recognize that the spring element of the device 450 could be a rubberized torsion spring or any similar component.

Figure 5B:
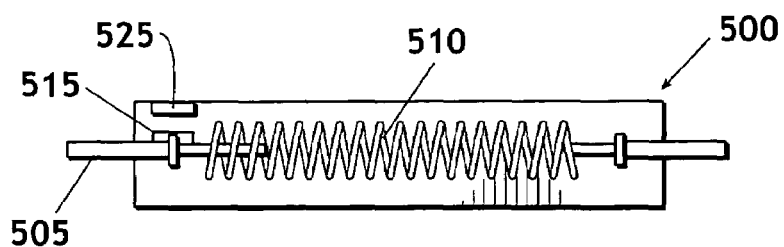
FIGS. 5A-5B illustrate a preferred embodiment of the instant invention which utilizes one or more coil springs internally.
Figure 5A:
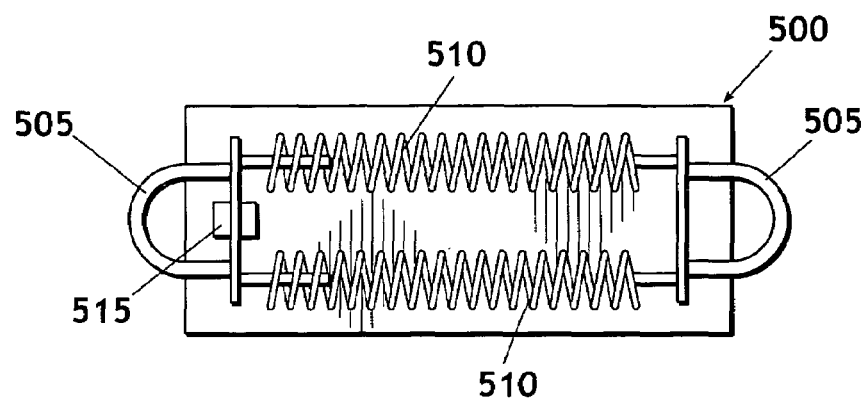

According to still another preferred embodiment, as is generally illustrated in FIG. 5, there is provided an invention similar in function to the embodiments described previously, but wherein there are one or more internal springs 510 which interconnect tie element 505. In the preferred embodiment, one end of the patient's vest belt 410 will be attached to one tie element 505 and the other tie element 505 will be connected by a separate belt or lead to the bed frame or other immobile object. Thus, when the patient exerts tension on the belt 410, the springs 510 will be drawn apart, thereby separating the sensor pair 515, 525. Assuming that the springs 510 have been properly sized, it is expected that, as a general rule, a patient will not be able to accidentally or intentionally trigger an alarm condition because of the strength necessary to maintain the switch in an open position. In one preferred embodiment, the instant device 500 will be configurable to engage either one, the other, or both of the springs 510, thereby providing a sensor that is potentially adjustable to at least three different threshold levels and making it possible to customize the response of the sensor depending on the amount of pull which it is envisioned it would be necessary to prevent false alarms. Note that the springs 510 need not be the same size.

Figure 6:
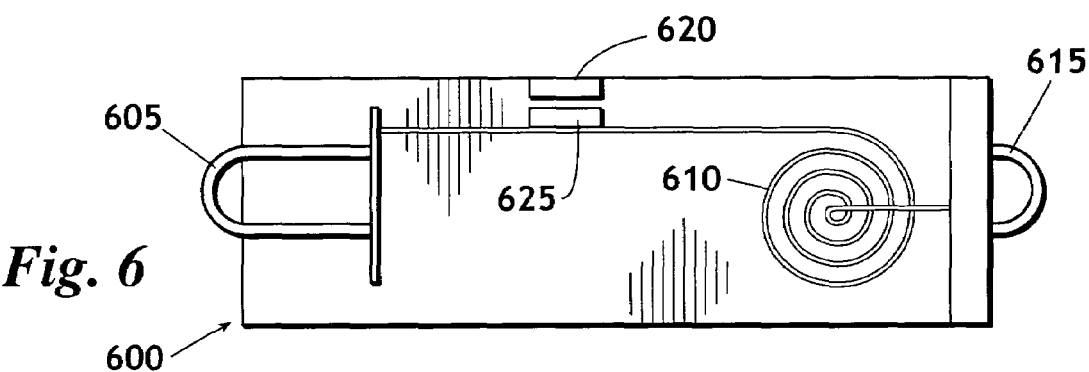
FIG. 6 is a schematic diagram of a preferred embodiment which utilizes an internal spring as a method of measuring tension on a restraint or other belt.

According to still another preferred embodiment and as is generally set out in FIG. 6, there is provided a device 600 which utilizes a coiled spring 610 or similar device to determine when the patient has placed tension on the belt 410. As is generally indicated in FIG. 6, in this preferred arrangement one half of the sensor pair 625 is attached to spring 610 and the other half 620 is affixed to the wall of the device 600. Thus, when pressure is exerted on belt 410 which is attached to tying element 605, the tying element 605 will move outward pulling spring 610 and unwinding it in much the same way as a measuring tape is unwound under tension. Such tension will separate the sensor pair 620/625 thereby making it possible for an attached electronic patient monitor to determine if the patient is under duress. As has been explained previously, the tension on spring 610 will be selected so that the patient cannot easily accidentally (or even intentionally) generate a false alarm. When tension is released from the belt, the tie element 605 will move back towards spring 610, thereby bringing the sensor pair into close proximity again.

Figure 7:
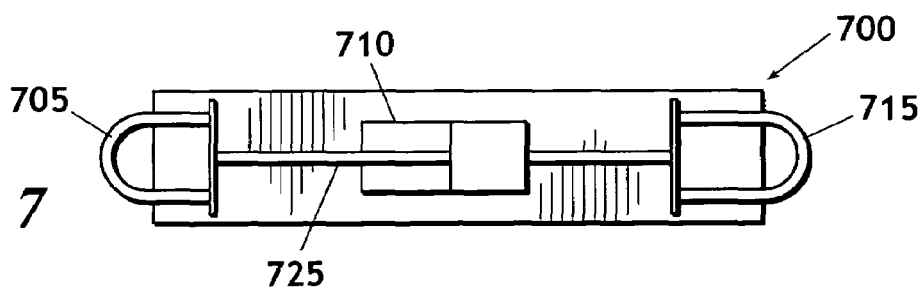
FIG. 7 contains a preferred embodiment wherein a piston or similar device provides a retarding force against which to measure the tension on a patient restraining belt.

Turning next to the preferred embodiment of FIG. 7, there is provided an invention substantially as described above but wherein the restoring/opposing force is provided by piston 710. Tie element 705, when attached to belt 410, will move outward under tension, thereby compressing the left half of cylinder 710. Of course, any number of compressible media might be placed inside cylinder 710, but air is the preferred media. Not shown in this figure is a sensor pair which would indicate when the piston is abnormally extended. Those of normal skill in the art will be readily able to devise such a sensor based on a measurement of the extension of rod 725 or some other measure (e.g., fluid pressure in the left half of cylinder 710). Of course, by reversing the orientation of the cylinder, increasing levels of vacuum (rather than increasing amounts of pressure) could be used as an indication of abnormal tension in the attached strap. Finally, in still another preferred arrangement instead of closed cylinder 710 a compressible bladder would be employed. As an example, a donut-shaped bladder might surround rod 725 so that movement of the tie element 705 would cause a plate that is affixed to the terminus of the rod 725 to exert pressure against the donut bladder. The amount of stress on the attached strap might be measured, for example, by determining the size of (or pressure within) the donut-shaped bladder.

Figure 9A:
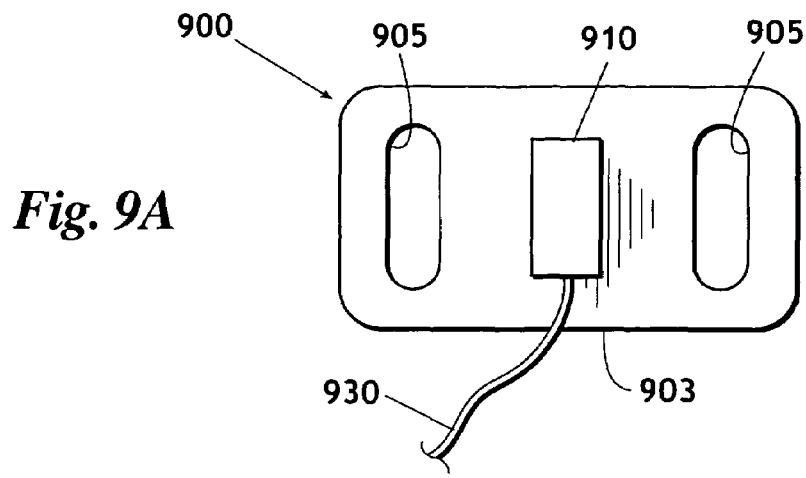
FIGS. 9A-9B contain another preferred embodiment which activates in response to the compressional force of a belt threaded therethrough.

There is set out in FIG. 9 still another preferred embodiment of the instant invention. In this variation and as it appears in plan view in FIG. 9A, tension monitor 900 contains a rigid base 903 surmounted by a pressure sensitive switch 910/925 which is preferably placed in electronic communication with a separate electronic patient monitor via electrical line 930. Apertures 905 are provided so that a restraining belt 915 can be threaded therethrough. Note that FIG. 9A illustrates this embodiment in plan view as it would appear without the restraining belt 910 in place.

Figure 9B:
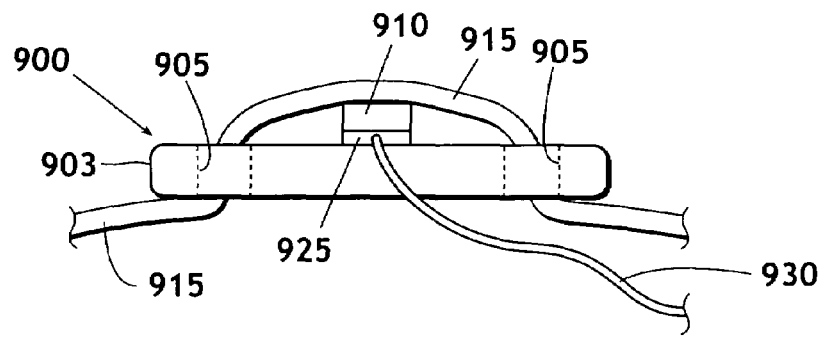

FIG. 9B illustrates the device of FIG. 9A as it would appear in a side view after a belt 915 has been threaded therethrough. As is illustrated in this figure, a belt 915 from the restraining vest has been threaded through the apertures 925 and, as has been described previously, it is expected that the remote end of the belt 915 will be tied or otherwise attached to an immobile object. Switch 925 is preferably a membrane-type switch and is preferably surmounted by an elastic block 910 or similar resilient member. For example, the block 910 might be made of rubber, polyurethane, foam rubber, etc. It is preferred that the block 910 has some amount of elastic rebound or resiliency.

In operation, when tension is placed on the belt 915 it will bear downward on elastically resilient element 910 which, in turn, will apply pressure to switch 925 and will cause the switch 925 to engage at some level of belt tension 915. It should be clear to those of ordinary skill in the art that the threshold level at which the switch 925 engages can readily be varied in any number of ways including, for example, by varying the stiffness or hardness (as determined, for example, by a durometer) of elastic component 910, by changing the contact area between the elastic component 910 and the switch 925, by selecting a switch 925 of different stiffness, etc. Then, if the patient exerts sufficient tension on the belt 915 to engage the switch 925, an attached electronic patient monitor (not shown) will note that fact and respond accordingly. It is anticipated that the programming of the monitor will be designed to help it differentiate between intermittent and sustained engagement of the switch 925 so that the likelihood of false alarms can be reduced. Additionally, it should be noted that elastic component 910 is not strictly necessary, as it would be possible to use the elastic rebound of the switch 925 by itself, i.e., have the belt directly engage switch 925, if that were desired.

Figure 11:
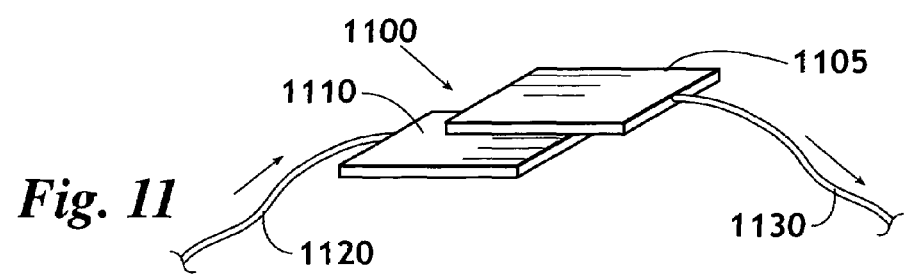
FIG. 11 illustrates how two optically transmissive plates may be used to determine an amount of offset.

Turning next to FIG. 11, there is provided a preferred sensor 1100 which can be used to determine when a restrained patient is in distress. By way of general explanation, optically translucent or transparent plates 1105 and 1110 are placed into proximity with each other. A light source is placed into optical communication with optical conduit 1120, which carries the light to lower plate 1110. Some portion of the light entering plate 1110 will be radiated to plate 1105 and captured for transmission through optical conduit 1130 to a waiting optical receiver. Further, the amount of light/intensity of the light that is transmitted through conduit 1130 will be a function of the degree to which the upper 1105 and lower 1110 plates overlap, with maximum optical transmission occurring when the two plates are same sized and positioned one directly above the other. Clearly, it is possible to calibrate this switch so that, depending on the output optical signal transmitted through conduit 1130, the amount of overlap of the two plates 1105 and 1110 can be determined and, hence, the relative amount of displacement between the two plates. Of course, the amount of displacement can then be related to the amount of stress that is being applied to the attached strap. Note that sensor 1100 would be suitable for use, by way of example only, with the embodiment of FIG. 5 (i.e., as sensor pair 515/525).

Figure 12:
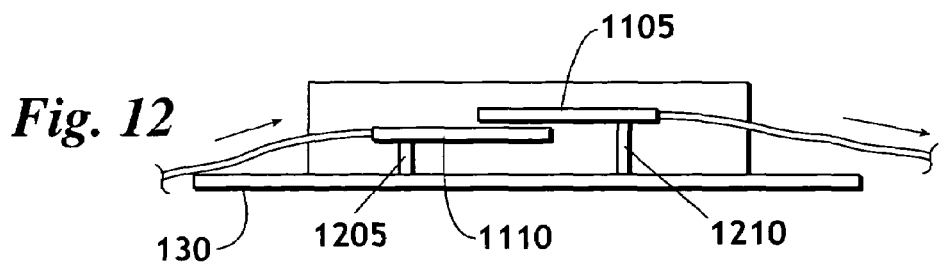
FIG. 12 contains a preferred embodiment of the invention of FIG. 11.

FIG. 12 illustrates how this switch 1100 can be used to determine the tension in a belt of a patient restraint device. As is generally illustrated in this figure, the plates 1105 and 1110 will be separately affixed at two different points of the belt 130 while the 130 belt is not under tension. When the belt 130 comes under tension, it will tend to elongate by stretching (most such belts are made of cotton or similar materials), thereby widening the spacing between the plate supports 1205 and 1210 and reducing the amount of overlap between the two optically transmissive plates 1105 and 1110. Then, by monitoring the intensity of the light passing through the switch it will be possible to determine the amount of stretching in the belt 130 and, hence, the amount of tension experienced thereby. It should be clear that other variations of this idea could certainly be employed including, for example, an arrangement as simple as a light source/sensor combination on opposite sides of sliding orifices, wherein the amount of light received is proportional to the amount of overlap between the orifices and the overlap is, in turn, related to the tension on an attached strap or belt.

Finally, and as has been described previously, extended periods of tension on the belt will be interpreted by the attached patient monitor 50 as being indicative of a patient in distress. By way of example, one test of a popular brand of patient restraint indicated that the application of 60 pounds of force on a one-foot section of one of its straps produced a lengthening of about 0.7 inches, which amount of deformation is readily measurable via a wide variety of techniques well known to those of ordinary skill in the art.

Figure 8:
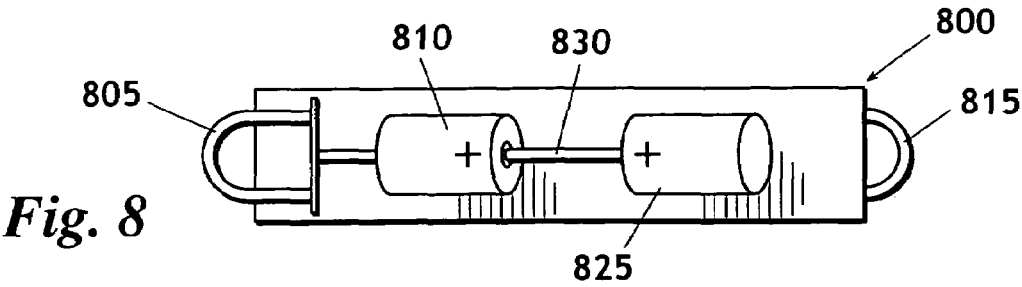
FIG. 8 illustrates a preferred embodiment of the instant invention which illustrates how magnetic resistance could be used to form a sensor suitable for use with the instant invention.

Turning next to FIG. 8, there is provided another spring-type embodiment 800 in which the restoring force is provided by same-polarity poles of magnets 810 and 825. As is set out in this figure, preferably rod 830 is threaded through stationary magnet 810, which rod 830 terminates in movable magnet 825. When tension is applied to a belt or a strap that is affixed to loop 805, that will tend to draw closer together the two magnets 810 and 825 which will resist such force because of their like polarities. As has been described previously, loop 815 will be affixed to a stationary object, preferably via a strap-type connection. By measuring the separation distance between the two magnets 810 and 825, it will be possible to determine the amount of tension applied to the attached belt and, hence, the status of the patient. Those of ordinary skill in the art will recognize how such an arrangement may easily be calibrated.

Figure 13:
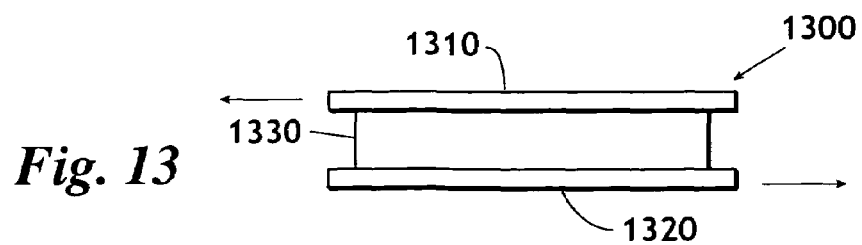
FIG. 13 illustrates another preferred embodiment, wherein tension on a belt or strap is measured by shear of an elastically deformable member.

FIG. 13 contains still another preferred embodiment, wherein shearing force is utilized to determine the tension on a belt or strap of a patient restraint device. In this embodiment 1300, upper plate 1310 is made to be relatively immobile with respect to movements in the attached strap. Lower plate 1320 is then affixed to the strap, so that any tension that is applied to the belt will result in a shearing force with respect to these two members. Connecting member 1330 is preferably a relatively stiff resilient or elastic element that resists the application of such shear (e.g., foam rubber, plastic, elastic, etc.). The amount of shear in the device 1300 may readily be measured by any number of means including, by way of example only, measuring the conductivity (electrical or optical) measured across the connecting member 1330, measuring the vertical distance that separates the two plates 1310 and 1320, measuring the lateral distance/amount of offset between the two plates caused by the applied force, measuring the magnetic or electrical field as a function of the amount of separation between the plates 1310 and 1320, etc.

Figure 14:
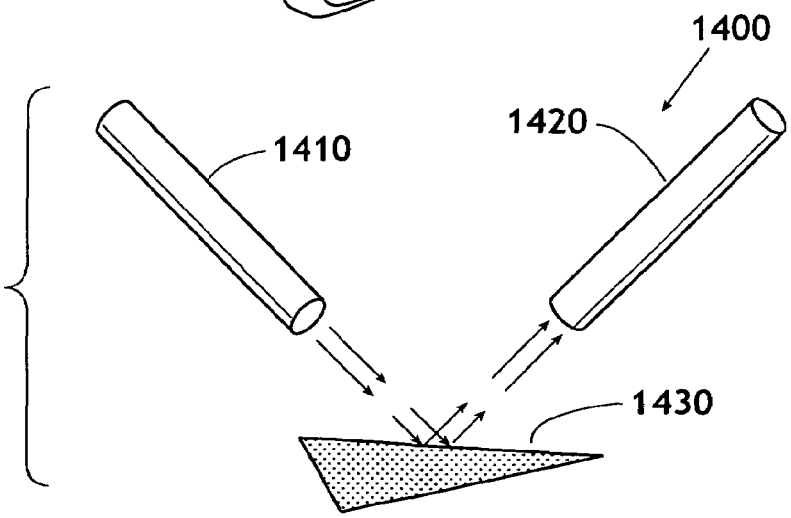
FIG. 14 contains a preferred embodiment which utilizes optical reflectivity to determine the amount of offset caused by tension on a restraining garment strap.

FIG. 14 contains still another preferred embodiment 1400, wherein the amount of tension on a belt or strap is determined by measuring the amount of movement of an optical target. As is generally indicated in FIG. 14, an optical conduit 1410 provides a light source which preferably bears on target 1430. A second optical conduit 1420 preferably receives light returning from the target 1430 and conveys it to a sensor which might determine, by way of example, the intensity or frequency content of the reflected light. In the example of FIG. 14, as the triangular target 1430 moves with respect to the light source, the intensity of the reflected light will vary as less (or more) of the black target 1430 fills the field of view of the receiver 1420. Thus, if the optical conduits that correspond to the source 1410 and receiver 1420 are held relatively stationary with respect to the monitored strap or belt and the target 1430 is allowed to move therewith as tension is applied to the belt, such movement will be interpreted in terms of amount of tension or stress applied to the belt. Those of ordinary skill in the art will recognize this is just one of many optical schemes for measuring displacement that could be used including, without limitation, optically sensing the movement of a series of printed tic marks (e.g., as in a ruler), various symbols passing in sequence under the light source (possibly of different color), etc. The ability to devise optical devices that measure relative displacement is well known within the art. Methods of then relating a measured displacement to the amount of tension or stress that is applied to a monitored object are similarly well known.

It should be noted that the instant invention utilizes tension on one or more straps of a restraint as an indicator of a possible patient emergency. However, for purposes of the instant disclosure, it should be understood that a measurement of belt "tension" should be broadly interpreted to include direct measurements of the amount of force being exerted longitudinally against the strap (e.g., the embodiment of FIG. 5) as well as less direct measurements such as those where tension is measured as pressure (e.g., FIG. 9), changes in the physical dimensions of the strap (e.g., changes in its length, width, etc., e.g., FIG. 12), etc. Still further, in some instances it might be possible to measure the tension on the strap or belt indirectly, e.g., by monitoring the amount of stress or pressure experienced by the patient on the inside of the vest or other restraint device. Similarly, measurement of the tension on the outside of the restraint device (e.g., on its exterior surface) could also be such an indirect indicator of tension. Those of ordinary skill in the art will certainly recognize that when tension is applied to a strap of a restraint device that tension is communicated to the restraint device itself through the attachments of the strap to the restraint. Thus by measuring the tension (or pressure, stress, etc.) on or in the vest an indirect measurement may be obtained of the tension on the strap and, hence, the circumstances of the patient. Thus, for purposes of the instant application, it should be understand that when a measurement is made of "a value representative of the tension" that phrase should be broadly construed to include measurements that might be taken directly from the strap itself or from any other element of the restraint device in mechanical communication with it.

Figure 10:
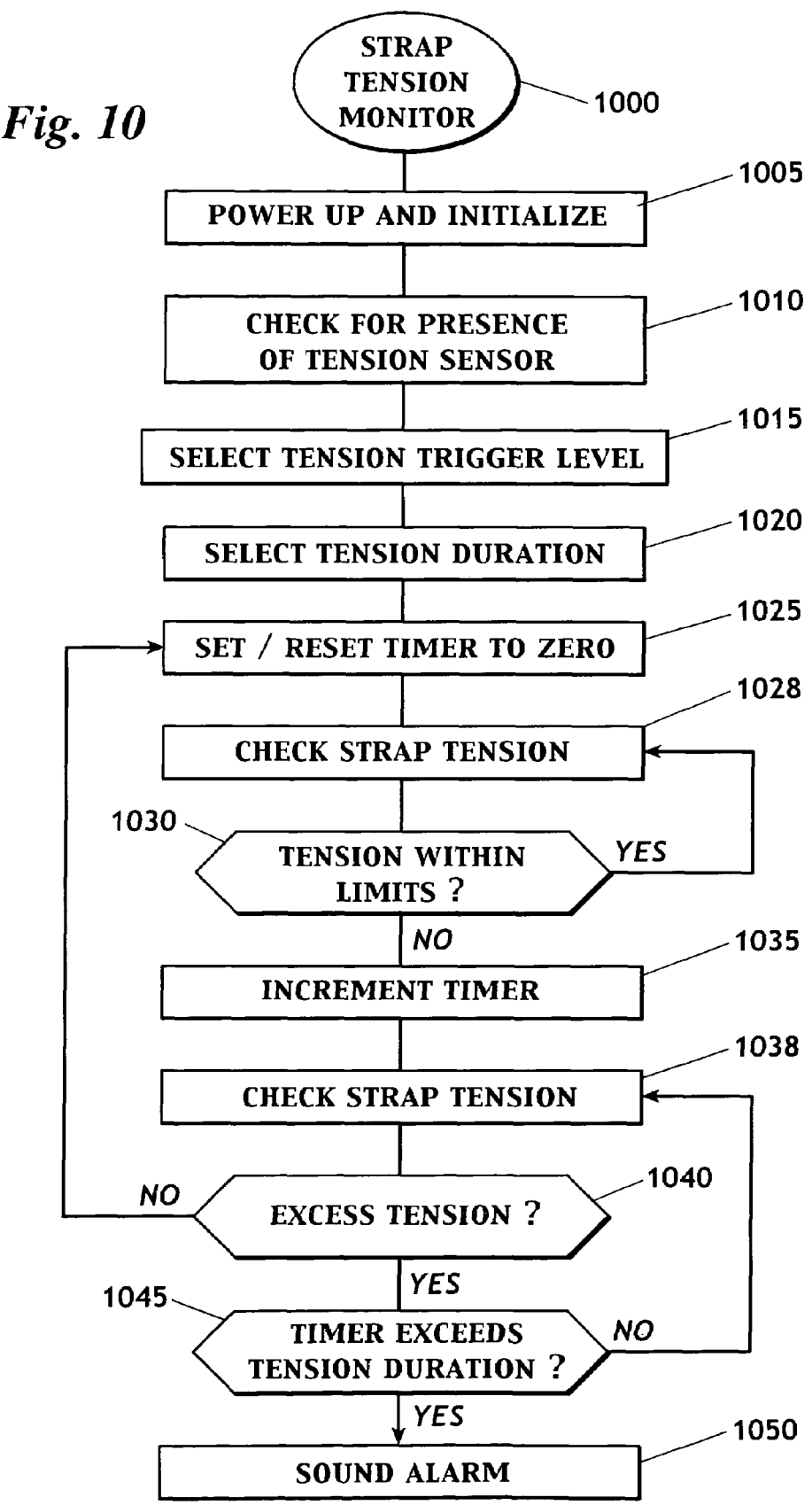
FIG. 10 contains a preferred operating logic for use in an attached patient monitor.

In practice, it is anticipated that each of the above-described embodiments will be placed into communication (e.g., electrical, optical, or wireless communication) with a separate electronic patient monitor 50. Preferably, the monitor will contain a microprocessor or similar hardware which can be programmed in some sense to respond to the status of the switch 100. FIG. 10 contains a preferred operating logic 1000 for use with such a microprocessor. Preferably, the monitor 50 will be powered up and its internal program variables initialized (step 1005). Note that the unit 50 might be manually powered up or automatically powered up upon the detection of an attached sensor 100. As a next preferred step 1010, and if this has not been done so already, the internal logic will verify that there is an attached sensor that is readable by the monitor.

Next, a tension trigger level will preferably be selected (step 1015). Although this step will not be necessary in every case, in those embodiments where a semi-continuous reading of the amount of tension on the strap is available (e.g., the embodiment of FIG. 11), it is preferable that some amount of flexibility be provided as to the alarm trigger point. Those of ordinary skill in the art will recognize that such adjustability would be especially desirable where the instant invention is used with patients of different sizes and weights. Additionally, the trigger level could be used to accommodate restraint belts that are of different stiffness, elasticity, etc. Note that the user may or may not be able to modify this parameter and, depending on the desires of the designer, it might be a factory preset value. Preferably, the trigger level will adjustable to correspond to strap tensions between about 30 and 60 pounds of pull.

As a next preferred step 1020, a tension duration will be selected. This parameter represents the length of time during which a continuous tension above the tension trigger level must be observed in order to trigger the alarm. This value is preferably a few seconds, e.g., one to fifteen seconds. One consideration that might impact the selection of this value is the need to reduce false alarms that are generated by patients who are merely restless, in which case the duration might be lengthened. This parameter might be either factory supplied as a fixed default or made to be adjustable depending on the desires of the designer.

As a next preferred step, a timer will be initilized to zero (step 1025). As is discussed below, this timer will be used to measure the amount of time that the strap remains under tension. Note that implementing such a timer does not require a discrete clock chip or other timing circuit, although that would usually be preferred. As is well known to those of ordinary skill in the art, simple software loops can readily be used to create a "clock" that would be suitable for the timings discussed herein.

Next, an event loop is entered which monitors the tension on the belt (steps 1028 and 1030). Preferably, this monitoring will be near-continuous, e.g., the attached switch will be read every one-tenth of a second or so. Alternatively, the switch might be configured such that excess tension generates an interrupt which wakes an attached monitor from sleep, in which case an event loop would not be needed. However, those of ordinary skill in the art will recognize how the second alternative could readily be implemented within the spirit of the instant invention.

In the event that the strap is not under abnormal tension, the program will branch back to step wherein the strap tension is measured (step 1028), preferably after waiting a predetermined period of time (e.g., a few tenths of a second).

However, in the event that abnormal tension is sensed, the timer will be incremented (step 1035) and a loop will be entered (steps 1038, 1040, and 1045) which preferably continues until either tension is released from the strap (the "NO" branch of step 1040) or until the incrementing timer exceeds the tension duration set previously (decision branch 1045), in which case the alarm will sound (step 1050).

As is broadly suggested in FIG. 10, in most cases the alarm will continue to broadcast until it is manually terminated, at which time presumably the patient will receive an in-person inspection from the caregiver. However, in order to reduce the occurrence of false alarms, in some cases it might be desirable to terminate the alarm broadcast automatically if the patient is not in distress. One preferred method of doing this is to continue to sound the alarm until the tension on the monitored strap or straps decreases to below a reset threshold for some period of time. That is, in a typical operating scenario the attached monitor will note that the tension on a strap exceeds the selected triggering threshold for the selected period of time. The alarm will begin to sound and will continue until either it is terminated manually or until the tension on the triggering strap falls below a predetermined reset threshold and, optionally, stays below the reset level for some period of time. In the preferred arrangement the reset threshold will be about one-half of the triggering threshold. Thus, if the tension is lowered sufficiently for a predetermined period of time greater than or equal to zero seconds, in this preferred embodiment the alarm will cease and the electronic monitor will return to monitoring the tension on the strap or straps. Of course, the reset threshold will generally be less than or equal to the triggering threshold and will preferably be greater than zero.

Those of ordinary skill in the art will recognize that there are many active devices that could serve for purposes of the instant invention as active portion of the patient monitor including, of course, a conventional microprocessor. More generally, the instant invention preferably includes an electronic monitor that utilizes some sort of active device, i.e., one that is programmable in some sense, is capable of recognizing signals from an attached patient sensing device, and is capable of initiating alarm sounds in response to a patient condition, such alarm sounds being transmitted to an internal, external, or remote speaker. Of course, these sorts of modest requirements may be satisfied by any number of programmable logic devices ("PLD") including, without limitation, gate arrays, FPGA's (i.e., field programmable gate arrays), CPLD's (i.e., complex PLD's), EPLD's (i.e., erasable PLD's), SPLD's (i.e., simple PLD's), PAL's (programmable array logic), FPLA's (i.e., field programmable logic array), FPLS (i.e., fuse programmable logic sequencers), GAL (i.e., generic array logic), PLA (i.e., programmable logic array), FPAA (i.e., field programmable analog array), PsoC (i.e., programmable system-on-chip), SoC (i.e., system-on-chip), CsoC (i.e., configurable system-on-chip), ASIC (i.e., application specific integrated chip), etc., as those acronyms and their associated devices are known and used in the art. Further, those of ordinary skill in the art will recognize that many of these sorts of devices contain microprocessors integral thereto. Thus, for purposes of the instant disclosure the terms "processor," "microprocessor" and "CPU" (i.e., central processing unit) should be interpreted to take the broadest possible meaning herein, and it should be noted that such meaning is intended to include any PLD or other programmable device of the general sort described above.

Note also that even though a microprocessor-based monitor is the preferred configuration, those of ordinary skill in the art will recognize that discrete components could also be used to duplicate the necessary functionality. Thus, for purposes of the instant invention an electronic patient monitor should be understood to include both microprocessor and non-microprocessor devices.

Further, those of ordinary skill in the art will recognize that the "speaker" that is utilized by the instant invention could be any audio device, whether directly incorporated into the monitor or remotely situated at a nurses station, etc. The speaker might be a conventional cone-type speaker, a piezoelectric device, a buzzer, a magneto-strictive device, etc., i.e., any device capable of generating an audio output whether local to the monitor or remotely situated.

Returning now to FIG. 2, there is provided another preferred embodiment of the instant invention which acts independently of, or in conjunction with, the other embodiments discussed previously. That is, in one preferred arrangement a wheel chair 30 or similar support surface will be equipped with an attitude or tilt sensor 260 which can sense whether or not the chair is upright. Preferably, the sensor 260 will be attached to a support member of the chair 30 such as a back or seat strut. It will preferably be connected electronically to monitor 250 by conduit 265. In the embodiment of FIG. 2, note that the single electronic patient monitor 250 is designed to accommodate both an exit sensor 200 and a tilt sensor 260. It further could include a port for tension sensor 100 if that were desired. Of course, separate monitors could also be used for each sensor.

Preferably the sensor 260 will be a mercury switch or similar electronic component that reacts to changes in its orientation with respect to vertical. Additionally, it is preferable that a two-axis (e.g., two mercury switches at right angles to each other and parallel to the ground) be used to avoid those situations that might not trigger a single switch. Those of ordinary skill in the art will recognize that there are any number of conventional inclinometers and inclinoswitches (attitude indicators), accelerometers (including multi-component accelerometers), etc. that could be used by an attached electronic patient monitor to determine when a chair is not vertically oriented. As a consequence, it should be remembered that when the term "inclinometer" is used herein, that term should be broadly interpreted to include any sensor (whether mechanical, electro-mechanical, electrical, optical, etc.) that is capable of generating signals representative of the orientation of the wheelchair and that makes it possible for an electronic patient monitor to determine whether or not the chair is in an upright position.

Preferably monitor 250 will be designed to respond to chair tipping events by sounding an alarm which might be from an integrated speaker or via a remote speaker. Such alarm will indicate to the caregiver that the patient may be in distress.

In still another preferred arrangement, the inclinometer 260 will be used with one of the restraint device belt tension sensing embodiments discussed previously. That is, in addition to monitoring the tension in a wheelchair patient's restraint device ties, the instant invention will preferably also monitor the orientation of the patient's chair. Then, as has been described previously, if the chair tips over the inclinometer 260 will respond to its new orientation and the attached patient monitor 250 will sense that fact and generate an alarm. However, if excess belt tension is also noted, that might indicate a situation that is life threatening and, for example, a more strident alarm might be sounded, an emergency situation might be signaled via a wireless transmitter in the monitor 250, etc. Those of ordinary skill in the art will recognize that many other variations of the instant invention may readily be devised.

Figure 15A:
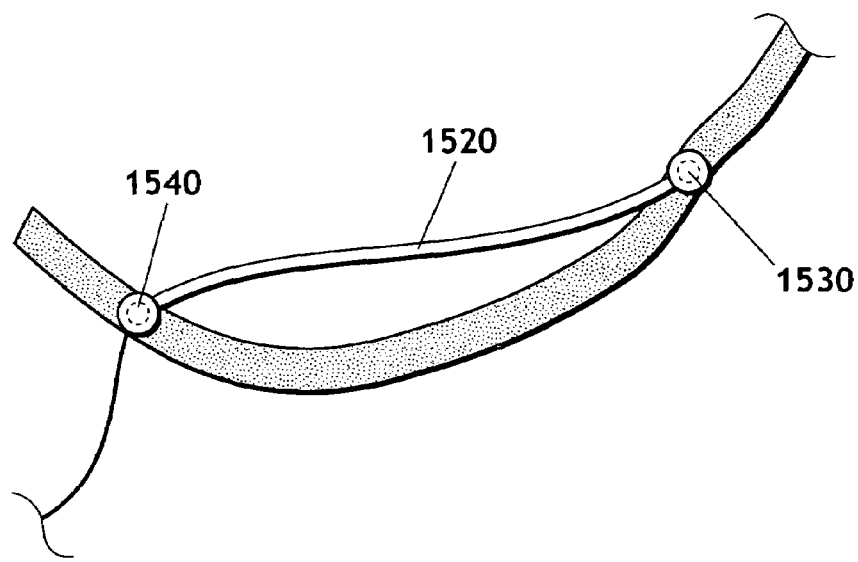
FIGS. 15A-15B contain another preferred embodiment of the instant invention which utilizes an elongate elastic member to determine when a strap is under tension.

Finally, in a further preferred embodiment there is provided in FIGS. 15A and B a sensor for detecting excessive levels of stress in a restraint device strap. As should be clear from this illustration, preferably the instant sensor will be comprised of a length of connecting material 1520 which is preferably elastic tubing or other elongate elastic material that is attached at two spaced apart points 1530 and 1540 of the strap 1550. As long as there is no stress (or minimal stress) on the strap 1550, the elastic nature of the connecting material 1520 will tend to draw the tends 1530 and 1540 toward each other, thereby creating a loop in the strap 1550. The length of the connecting material 1520 might be measured in many ways depending on the sort of material used. For example, if the connecting material 1520 is formed from surgical tubing or a similar elastic material the resistance as measured between 1530 and 1540 could be calibrated to give a good length estimate, with the decreasing cross section and increasing length during extension combining together to increase the overall resistively of this element.

Figure 15B:
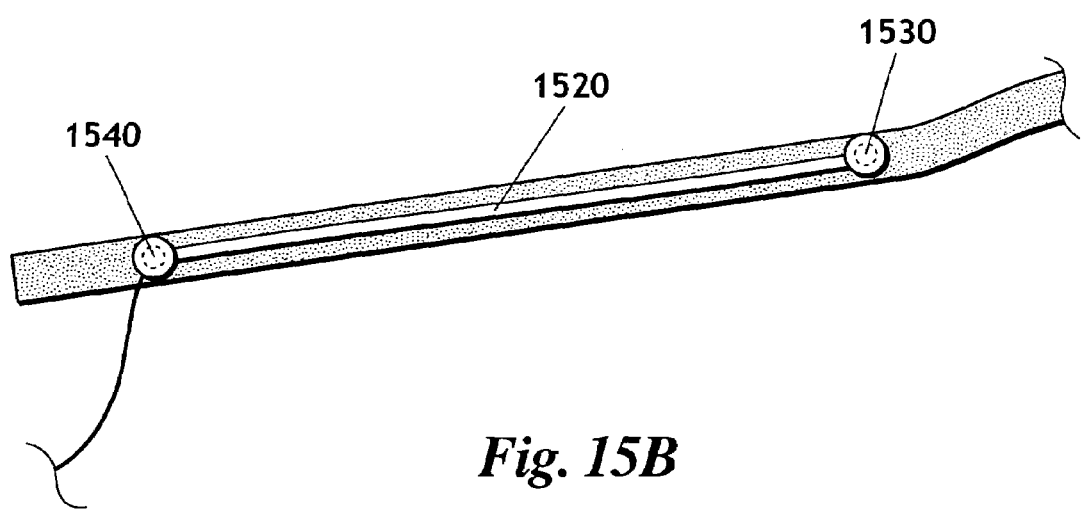

However, when stress is applied to the strap 1550, it will tend to be drawn into a linear configuration (FIG. 15B), thereby stretching the connecting material 1520. By monitoring the length of the attached connecting material 1520 (or monitoring any related parameter as is discussed below) it should be clear that some estimate of the amount of tension on the strap 1550 may readily be obtained. Note that in some preferred embodiments, the connecting material 1520 will be designed to be readily removed and reinstalled. This would permit the caregiver to adjust the sensitivity of the device to match the size and/or strength of the patient (e.g., by using stiffer or less elastic materials when heavier/stronger patients are restrained). Further, in some instances multiple elastic elements 1520 might be utilized as a means of increasing the triggering threshold of this device.

Finally, although measuring the length of the connecting material is a preferred means of determining whether or not stress has been applied to patient's restraining straps, those of ordinary skill in the art will recognize that there are certainly many other methods of making this determination. The preferred methods include measuring the air pressure inside of the connecting material 1520 (assuming, of course, that an air-impermeable material such as elastic tubing has been utilized as the connecting material 1520), measuring the resistively (or capacitance, etc.) of the connecting material 1520 as a function of its length (with increasing length tending to increase the resistance of the material 1520), measuring the magnetic flux where a magnet that moves as the material 1520 expands/contracts has been installed inside of an elastic tube and a corresponding fixed sensor measures the flux density, etc.

CONCLUSIONS

Those of ordinary skill in the art will recognize that there are an enormous number of ways of detecting and/or quantifying the amount of tension that is present in a belt or strap from a patient restraint device. For example, by placing a conventional strain gauge directly on the belt (or in physical communication with it) it would readily be possible to determine the amount of deformation of the belt under pressure and, to the extent such deformation can be related back to force, at least a crude measure of tension can be determined. As another example, if a piezoelectric element is subjected to the tension experienced by the belt (whether by directly connecting it to the belt or incorporating it within one of the embodiments described previously), the presence of excess tension in the belt can similarly be determined.

Additionally, it should be noted that there are many different detectors that could be used with the embodiments described above in determining the amount of deformation or displacement in such devices in response to the application of tension to an attached strap. For example, sensor pair 620/625 (FIG. 6) might be designed to measure the change in inductance of the stretching springs 510, such inductance being an indication of the amount of tension placed thereon. Materials which change in electrical properties under tension—and the nature of those changes—are well known to those of ordinary skill in the art. Further, it should be noted that, broadly speaking, most methods of determining a change in length or separation could potentially be used to formulate sensors for use with the various embodiments of the instant invention. For example, linear potentiometers, field sensors, RF proximity, ultrasound distance, ultrasound proximity (e.g., determining the location of an object by measuring differential travel times, phase, etc.), light bounce (transit time, frequency change, intensity change, etc.), resistance, etc., could all also be used to measure either the displacement of the spring supports under tension and/or the amount of tension present in the springs. Clearly, these same technologies could also potentially be used to measure the changing length of a restraint strap or belt under tension.

Further, the instant disclosure has taught a variety of different embodiments that utilize springs as means of creating a force that is biased against/counter to the tension that a patient might place on a belt or strap including, of course, a conventional metallic helical torsion spring. This is, of course, not the only way to create an elastic force suitable for use with the instant invention, i.e., an elastic force that tends to oppose movement in the sensor when tension is placed on a restraint device strap. For example, a spring might be formed by using a block or strip of elastic (e.g., rubber) or other resilient material. In other instances the necessary spring tension will originate from the material that is used to form the sensing device. For example, the embodiment of FIG. 4E might be formed as a single solid "U"-shaped element with the necessary "spring" tension being provided by the inherent tendency of the material to maintain its shape. Thus, for purposes of the instant invention, when the term "spring" is used herein, that term should be construed broadly to include a conventional discrete spring element (whether metal, elastic, plastic, compressible fluid, vacuum, etc.) that tends to elastically resist tension that has been placed on the attached strap as well as well as those instances where there is no separate spring but the requisite elastic force is provided by the material that forms the switch.

Further, it should be noted that in the preferred embodiment each sensor will be adjustable to respond to different amounts of tension. Those of ordinary skill in the art will recognize that a 300 pound person who is being supported by the restraint straps will cause substantially more tension in the straps than a 100 pound person who is similarly suspended. As a consequence, some method will preferably be provided for the caregiver to adjust the stiffness of the spring component in those embodiments that utilize a discrete spring. For example, in the embodiment of FIG. 6, the tension in the spring 610 could increased/decreased by winding/loosing it about its central support. In other embodiments, alternative springs will be provided that are to be used with different size patients (e.g., the spring 510 might be made to be user replaceable). In some embodiments the user will be allowed to adjust the spring coil count within, for example, the embodiment of FIG. 5, thereby adjusting its tension. Additionally, or alternatively, and as has been discussed previously, the threshold tension necessary to trigger an alarm event will preferably be made to be modifiable by the caregiver. In the preferred arrangement, the caregiver will be able to digitally select a tension threshold to match the needs of each patient (whether that threshold is expressed in units of force or via a "high/medium/or low" ordinal scale, etc.). Of course, a properly chosen threshold will help reduce the risk of false alarms while ensuring that the alarm is sounded when a lighter patient is in danger.

Note that it is preferred that the instant invention monitors the tension in a restraint strap in a near continuous manner, e.g., every second or more frequently. That being said, those of ordinary skill in the art will recognize that the frequency with which the strap is monitored is unimportant to the operation of the instant invention, although clearly more frequent monitoring will likely be preferred.

Although the restraint device that has been used for purposes of illustration has been a poncho-type restraint, those of ordinary skill in the art will recognize that there are many alternative restraint devices that would also be suitable for use with the instant invention. For example, some patients have their arms and/or legs restrained by means of by means of straps that are individually attached to the bed frame. In such a case, separate sensors could be utilized on each strap (or, alternatively, on a subset of them). However, in such instances it is preferred that a single electronic patient monitor with multiple input ports be used to monitor the status of all such straps. Further, and this is especially true of restraint devices like the vest 125 of FIG. 3, in some instances it is contemplated that multiple straps might be monitored by a single tension sensor. That is, and using as an example the vest 125, when this vest 125 is placed on a patient, two of its straps are intended to be affixed on the left and two others are affixed on the right. In such a configuration, both left-side straps could be tied to the same tie element (e.g., tie element 505) or both could be threaded through a single sensor (e.g., sensor 400). Those of ordinary skill in the art will recognize that many similar variations could readily be devised.

It should further be noted that the term "nurse call" as that term has been used herein should be interpreted to mean, not only traditional wire-based nurse call units, but more also any system for notifying a remote caregiver of the state of a patient, whether that system is wire-based (e.g., fiber optics, LAN) or wireless (e.g., R.F., ultrasonic, IR link, cell phone, etc.). Additionally, it should be clear to those of ordinary skill in the art that it may or may not be a "nurse" that monitors a patient remotely and, as such, nurse should be broadly interpreted to include any sort of caregiver, including, for example, untrained family members and friends that might be signaled by such a system.

Finally, it should be understood and remembered that when the term "tie element" is used herein that term should be broadly construed to include any point of contact between a belt, strap, band, etc., and the tension sensor, whether that contact is held in place by an actual tie, Velcro®, etc., or whether it is permanently affixed. Further, note that one tie element might be directly connected to the immobile object without the use of an intervening strap, band, etc. Generally speaking, the purpose of the tie element is to provide mechanical communication between the restraint device, the elastic element at the core of the tension sensor, and the immobile object. Thus, when "tie element" is used herein, that phrase should be broadly interpreted in the sense described above and not limited to interconnections/attachments that require an actual "tie" or other removable means of engagement.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A method of monitoring a patient who is restrained by a restraint device, said restraint device having at least one strap for attachment to a stationary object, comprising:
   (a) selecting at least one of said at least one straps for attachment to a stationary object;
   (b) selecting a tension threshold;
   (c) selecting a tension duration;
   (d) measuring a value representative of a tension in said selected at least one strap;
   (e) performing step (d) until said measured representative value equals or exceeds said selected tension threshold;
   (f) if said measured representative value equals or exceeds said selected tension threshold,
      (f1) repeatedly measuring a then-current value representative of a tension in said selected strap for a period of time at least equal to said tension duration,
      (f2) if during said measurements of step (f1) none of said measured then-current values is less than said tension threshold, sounding an alarm, else, continuing to perform steps (d) and (e) as needed, thereby monitoring the patient who is enclosed within said restraint device.

2. A method of monitoring a patient according to claim 1, wherein said tension duration is between about 1 and 15 seconds.

3. A method of monitoring a patient according to claim 1, wherein step (d) comprises the step of:
   (d1) in said selected at least one strap, measuring a value representative of a tension therein.

4. A method of monitoring a patient who is restrained by a restraint device, said restraint device having at least one strap for attachment to a stationary object, and wherein is provided a tension duration greater than zero, comprising:
   (a) selecting at least one of said at least one straps for attachment to a stationary object;
   (b) selecting a tension threshold;
   (c) measuring a value representative of a tension in said at least one selected strap;
   (d) performing step (c) until said measured value equals or exceeds said selected tension threshold; and,
   (e) if said measured value continues to equal or exceed said selected tension threshold for at least a period of time equal to said tension duration, sounding an alarm.

5. A method according to claim 4, wherein is provided a reset threshold, and wherein step (e) comprises the steps of:
   (e1) for a predetermined period of time at least equal to said tension duration, repeatedly measuring a then-current value representative of a tension in said selected strap, and,
   (e2) if during said predetermined period of time of step (e1) none of said measured then-current values is less than said reset threshold, sounding an alarm, else, not sounding an alarm and continuing to perform steps (d) and (e) as needed, thereby monitoring the patient who is enclosed within said restraint device.

6. A method according to claim 5, wherein is provided a reset time, and wherein step (e2) comprises the steps of
   (i) if during said predetermined time period of step (e1) none of said measured then-current values is less than said reset threshold, sounding an alarm, else,
   (ii) if during said predetermined time period of step (e1), one of said measured then-current values is less than said reset threshold and,
      if subsequently measured then-current values do not remain less than said reset threshold for a period of time greater said reset time, sounding an alarm, else,
   (iii) if during said predetermined time period of step (e1), one of said measured then-current values is less than said reset threshold, and,
      if subsequently measured then-current values are all less than said reset threshold for a period of time greater then or equal to said reset time, sounding an alarm, else,
   (iv) continuing to perform steps (d) and (e) as needed, thereby monitoring the patient who is enclosed within said restraint device.

7. A method according to claim 5, wherein said reset threshold is about 50% less than said tension threshold.

8. A method of monitoring a patient who is restrained by a restraint device, said restraint device having at least one strap for attachment to a stationary object, comprising:
   (a) selecting one of said at least one straps for attachment to a stationary object;
   (b) selecting a tension threshold;
   (c) selecting a reset threshold less than or equal to said tension threshold;

(d) measuring a value representative of a tension in said selected strap;
(e) performing step (d) until said measured value equals or exceeds said selected tension threshold; and,
(f) if said value equals or exceeds said selected tension threshold,
   (f1) for a period of time at least equal to said tension duration repeatedly measuring a then-current value representative of a tension in said selected strap, and,
   (f2) if during said measurements of step (f1) at least one of said measured then-current values is less than said reset tension continuing to perform steps (d) and (e) as needed, else sounding an alarm, thereby monitoring the patient who is enclosed within said restraint device.

9. A method according to claim 8, wherein said reset threshold is about 50% less than said tension threshold.

10. A method of monitoring a patient according to claim 8, wherein step (d) comprises the step of:
   (d1) in said selected at least one strap, measuring a value representative of a tension therein.

* * * * *